United States Patent [19]

Carter et al.

[11] 4,114,188

[45] Sep. 12, 1978

[54] APPARATUS FOR INDICATING UTERINE ACTIVITY IN LABOR

[75] Inventors: Michael Charles Carter; Philip James Steer, both of London, England

[73] Assignee: National Research Development Corporation, London, England

[21] Appl. No.: 757,024

[22] Filed: Jan. 5, 1977

[30] Foreign Application Priority Data

Jun. 23, 1976 [GB] United Kingdom ............... 26042/76

[51] Int. Cl.$^2$ .......................... A61B 5/04; A61B 5/10; G06F 15/42
[52] U.S. Cl. .................................... 364/415; 128/2 S; 128/2.1 M
[58] Field of Search ............ 235/151.3; 128/25, 2.1 M

[56] References Cited

U.S. PATENT DOCUMENTS

| 3,520,294 | 7/1970 | Fuzzell et al. | 128/2 S |
|---|---|---|---|
| 3,606,879 | 9/1971 | Estes | 128/2 S X |
| 3,989,034 | 11/1976 | Hojaiban | 128/2 S X |

OTHER PUBLICATIONS

Instrument for Measuring the Contractile Activity of the Uterus, V. Pronin, Biomedical Engineering, vol. 7, No. 4, pp. 212-215, Jul.-Aug. 1973.

An Automated Method for the Frequency Analysis of Myoelectric Signals Evaluated by an Investigation of the Spectral Changes Following Strong Sustained Contractions, S. Johansson, L. E. Larsson & R. Ortegren, Med. & Biol. Engng., vol. 8, No. 3, pp. 257-264, 1970.

A State Variable Averaging Filter for Electromyogram Processing, Med. & Bio. Eng., vol. 10, pp. 559-560, 1972.

Primary Examiner—Edward J. Wise
Attorney, Agent, or Firm—Cushman, Darby & Cushman

[57] ABSTRACT

Apparatus for providing an indication of uterine activity in labor is described. Intrauterine pressure above the basal pressure existing between contractions is integrated over intervals of between ten and thirty minutes to give the required indication. An algorithm is disclosed for calculating dosage of a labor inducing substance, the algorithm containing safeguards to prevent hyperstimulation.

22 Claims, 18 Drawing Figures

APPARATUS FOR INDICATING UTERINE ACTIVITY IN LABOR

The present invention relates to apparatus for providing an indication of uterine activity in labour, and the apparatus may be extended to determine suitable dosages of labour inducing substances, that is substances which cause contractions to occur, such as for example oxytocin or prostaglandins.

The correct rate of infusion of oxytocin has mainly in the past been determined by observation of the frequency of contractions but this method suffers from the disadvantage that the rate of infusion may occasionally be too low to cause labour to continue or so high that the foetus is in danger.

In attempting to find a more accurate measurement of uterine activity other factors such as pressure, duration and profile of contractions have been measured.

Automatic apparatus for controlling oxytocin infusion is available but this apparatus operates by increasing the infusion rate until preset frequency and pressure values are reached. Such limits cannot take into account the wide variation in normal uterine activity and as a result inadequate stimulation appears to occur in approximately 4% of cases, but seriously gross stimulation appears to occur in 8% of cases. This hyperstimulation carries grave risks to the foetus.

According to the present invention there is provided apparatus for indicating uterine activity in labour including means adapted to be coupled to an intrauterine pressure transducer for providing a first signal representative of intrauterine pressure, means for providing a second signal which is equal to the first signal except when a contraction occurs when it takes up a value equal to that of the first signal in the absence of the contraction, means for subtracting the second signal from the first signal, to provide a third signal and means for integrating the third signal over intervals of at least ten but not more than 30 minutes to provide an activity signal indicative of uterine activity in labour.

Apparatus according to the invention may be used to calculate dosage of a labour stimulating substance if the apparatus includes dose calculating means for determining dosage in dependence at least upon the activity signal, the apparatus being such that when the dosage determined is employed, labour progresses without substantial interruption and without the said integral exceeding a dangerous value.

The main advantage of the present invention is that the said activity signal is a more satisfactory measure of uterine activity than other parameters which have been readily available before since the basal pressure, that is the pressure which occurs between contractions is subtracted before integration. However, one of the problems encountered in determining the said integral is that the basal pressure varies between contractions and also the pressure is often different before a contraction is compared with after. This problem is largely overcome by deriving the second signal and by subtracting the second signal from the first before integration.

Preferably each said integral is taken over about fifteen minutes, this being a compromise between sensitivity and the random changes due to the last contraction being just in or just out of the sample period.

The progress of labour can be determined by comparison of successive activity signals each obtained at the end of a fifteen minute interval. Hence the dose-calculating means may include a plurality of stores for storing digital values representing successive activity signals, and dosage, for example rate of infusion of oxytocin, can be determined, at least partially, from the relationship between successive activity signals.

In a typical induced birth the integral signal rises steadily and then reaches a "plateau" where further activity signals are slightly smaller in value than previous such signals. The present inventors have found that when the plateau region is reached dosage can be reduced by half, usually without materially affecting the progress of labour. The dose calculating means may therefore include a first comparator for comparing the current activity signal with a previous such signal and means for stabilising or preferably reducing, by for example half, the dosage when the value of the current activity signal is equal to, or smaller than, the former signal.

If the dosage is continually increased after the plateau has been reached the activity signal will eventually again start to rise in value and this is potentially dangerous. Thus, as a safety measure to prevent hyperstimulation, the means for determining dosage may include a second comparator for comparing the current activity signal with a first reference signal representative of hyperstimulation. The reference signal should be equivalent to a value of the said integral of between 1300 to 1800 kilo-Pascal seconds (kPas) and preferably 1500 kPas for a 15 minute integration integral and means are provided for decreasing the dosage, preferably by half when the second comparator indicates the reference signal has been exceeded.

On the other hand the activity signals may indicate that labour is not yet fully in progress and for this reason a third comparator may be provided for comparing the current activity signal with a second reference signal equivalent to between 300 and 800 kPas, preferably 500 kPas for a fifteen minute integration period. Means are then included for increasing the dosage in response to the output of the third comparator.

The dose calculating means may include a programmable read-only memory (PROM) coupled to the three comparators, where provided. A program entered into the PROM provides outputs on different terminals of the memory in accordance with the outputs of the comparators and outputs of the PROM fed back to indicate progress. In general the program may carry out tests for integrals exceeding 1500 kPas at various times in the program halving the dosage if this figure is exceeded; carry out tests for integrals below 500 kPas, increasing the dose when this figure is not exceeded; and increasing the dose steadily once every 15 minutes until the value of the current activity signal is below that of a former such signal when the dosage is halved.

The above mentioned means for increasing, stabilising and reducing the dose may thus be set up in the PROM by means of the program.

Means may be provided for entering a value into the dose calculator to set the dose to an initial value or another value decided on by different methods.

Indicator means may be provided for indicating the dosage determined and/or a signal from the means for determining dosage may be used as a control signal for controlling the rate of infusion of oxytocin.

Another aspect of the invention relates to the provision of a stable baseline when a waveform contains very low frequency components and normal AC coupling techniques cannot therefore be used. The contraction waveform has a variable basal pressure or datum and, as explained above, it is the provision of the third signal which allows the activity signal to be determined from a stable datum. However, there are many other applications where a corrected output signal from a signal having a variable datum is required.

Hence according to a further aspect of the invention there is provided apparatus for deriving a corrected signal from a signal with a varying datum, including means for receiving a first signal having a varying datum, means for providing a second signal which is equal to the first signal except when the first signal deviates from the datum when it takes up a value equal to that of the first signal in the absence of deviation, and means for providing a third corrected signal by subtracting the second signal from the first signal.

It will be recognised that the baseline connection circuits hereinafter described are examples of apparatus according to the second apsect of the invention. One example of the application of the second aspect of the invention is as follows: where it is required to provide an indication of the relationship between changes in intrauterine pressure and foetal heart rate, the absolute pressure is unimportant so that a guard-ring tocodynamometer (described by C.N. Smyth in the Journal of Obstetrics & Gynaecology of the British Commonwealth, 77, 908) may be used. Large fluctuations in the signal baseline often occur with resultant difficulties in chart recording and the baseline correction circuit may be used to reduce these fluctuations.

Certain embodiments of the invention will now be described, by way of example, with reference to the accompanying drawings, in which.

The embodiment of FIG. 1 will first be described in outline and then details will be given.

An electrical signal representative of intrauterine pressure is derived from the external socket of a commercially available cardiotocograph or an intrauterine pressure transducer and passed by way of a buffer amplifier 11 which drives a pressure indicating meter 12 to a baseline correction circuit 13. Since it is the integral of the areas of those parts of the pressure versus time curve (shown as the curve in FIG. 2a) which are above the basal pressure which is of interest, the baseline correction circuit 13 substitutes a steady baseline 14 in the curve of FIG. 2b for the varying basal pressure 15 in the curve of FIG. 2a. The corrected baseline 14 is at zero pressure and the corrected pressure signal is passed to an integrator circuit 16.

An alarm circuit 17 sounds an alarm if the catheter which forms part of the cardiotocograph becomes blocked and the pressure signal drops to around zero. The alarm also sounds if the basal pressure reaches an abnormal level for long periods.

Figure 1:
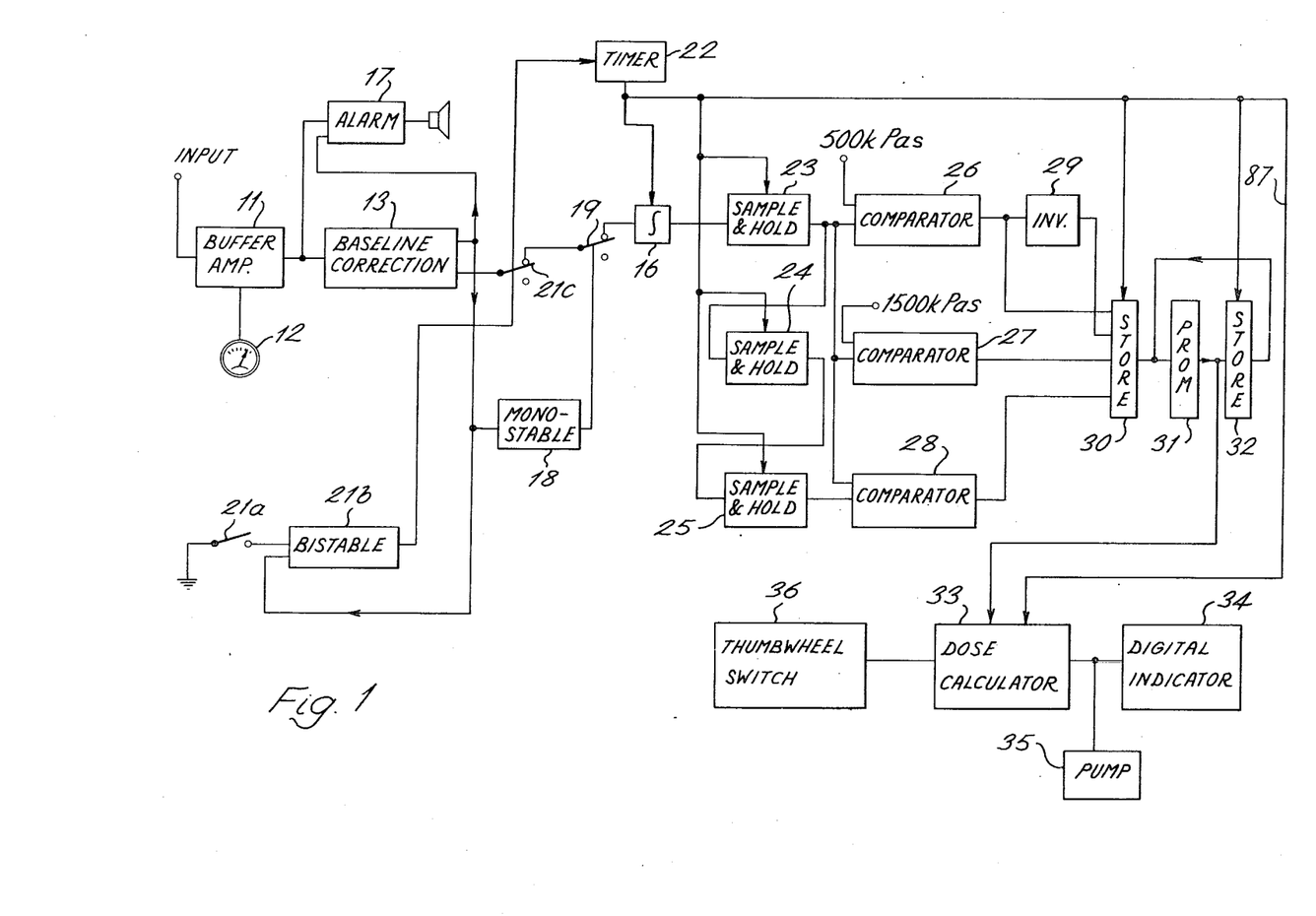
FIG. 1 is a block diagram of apparatus according to the invention.
Figures 2A, 2B:
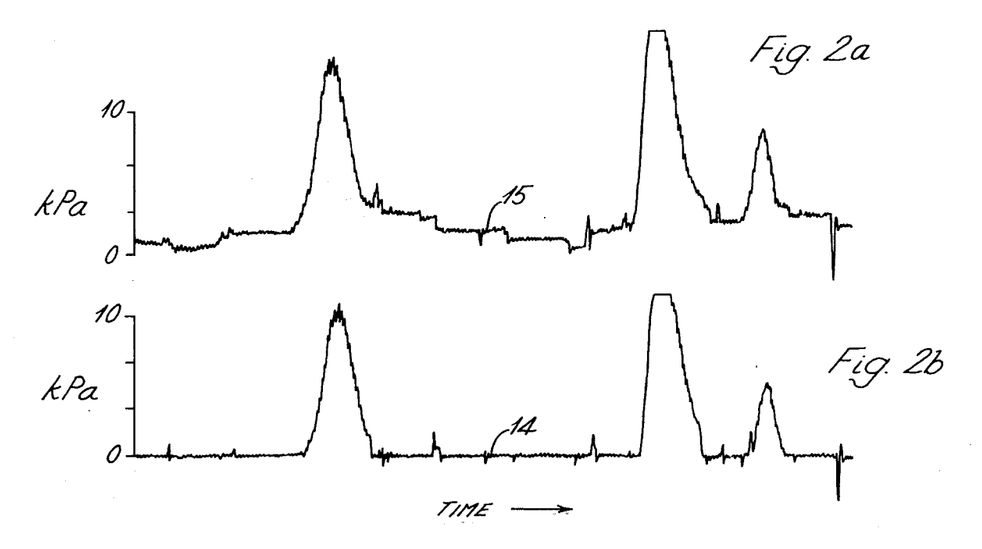
FIGS. 2a and 2b show graphs of pressure against time before and after application to the baseline correction circuit which forms part of the circuit of FIG. 1, FIGS. 3a and 3b are block diagrams of the baseline correction circuits which may be used in the circuit of FIG. 1, FIGS. 4a to 4g are waveforms of signals which occur in the apparatus of FIG. 1.

Both curves 14 and 15 of FIGS. 2a and 2b show artefacts of short duration and to prevent these artefacts from being integrated by the circuit 16 a monostable circuit 18 operates switch means 19 which momentarily disconnects the input to the integrator.

When the patient is placed on a bedpan a switch 21a is operated arresting a timer circuit 22 and operating switch means 21c to disconnect the input signal to the integrator.

At the end of a timing period of fifteen minutes as determined by the timer circuit 22 the integrated value at the output of the integrator 16 is sampled by a first sample and hold circuit 23 and at the same time the previous contents of the circuit 23 are passed to a sample and hold circuit 24, the previous contents of which are passed on to a sample and hold circuit 25. The values held by the circuits 23 to 25 which indicate the progress of labour as represented by the integrals are applied to three comparator circuits 26, 27 and 28. The comparator 26 gives a high output signal level when the integral value held by the sample and hold circuit 23 exceeds 500 kPas. This high output is applied to a store 30 and also to an inverter circuit 29 to give a high output at a separate terminal of the store 30 when the contents of the circuit 23 indicate an integral below 500 kPas. If the integral value held by the circuit 23 exceeds 1,500 kPas the comparator 27 provides a high output level which is also applied to a separate terminal of the store 30. The comparator 28 compares the contents of circuits 23 and 25 and when the output of the former is greater than the output of the latter a comparator 28 gives a high output signal applied again to a separate terminal of the store 30.

The various outputs of the comparators 27 and 28 as stored by the store 30 are applied to a PROM 31 and the output from the PROM is coded and fed back by way of a store 32 to the PROM input. The code fed back to the PROM input and the comparator states as indicated by the store 30 determine which outputs of the PROM will be high according to the program entered into the PROM. The output signals from the PROM are fed to a dose calculator 33 which at the end of each fifteen minute period either indicates that the dose should be increased or halved. The current dose levels are indicated by a digital indicator 34 and a pump 35 is coupled to the calculator so that its speed is proportional to the current dose. The motor drives a pump infusing oxytocin or oxytocin agents into the patient. A thumbwheel switch 36 is connected to the calculator 33 to allow any dose to be set on the switch and entered into the calculator.

Figure 3A:
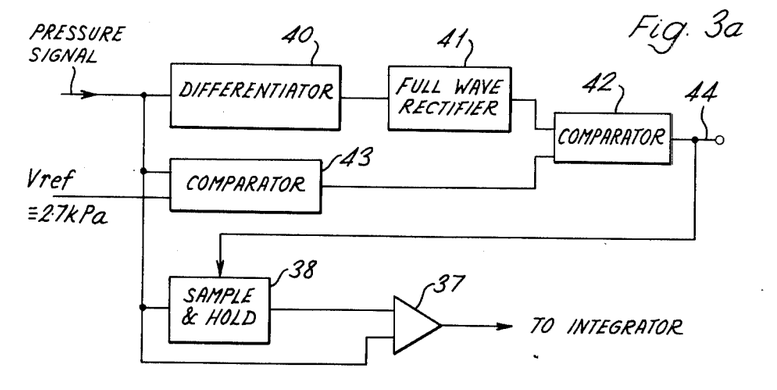

One form of the baseline correction circuit 13 is shown in more detail in FIG. 3a where the output of the buffer amplifier 11 is shown applied directly to one input of a differential amplifier 37 and by way of a sample-and-hold circuit 38 to another input of the amplifier. When the circuit 38 is in the "sample" mode both inputs to the amplifier are identical so the output from the amplifier (see the lower curve FIG. 2) which is passed to the integrating circuit 16 is zero, ignoring the effect of artefacts. At the onset of a contraction the circuit 38 is switched to the "hold" mode for the duration of the contraction. The output from the amplifier 37 is therefore the varying contraction signal minus the basal pressure signal which existed at the onset of the contraction. At the end of the contraction the circuit 38 is switched back to "sample" and its output returns to zero. The circuit 38 may be based on the National Semiconductor LH0022 series operational amplifier and constructed as set out in the manufacturer's data.

Figure 4A:
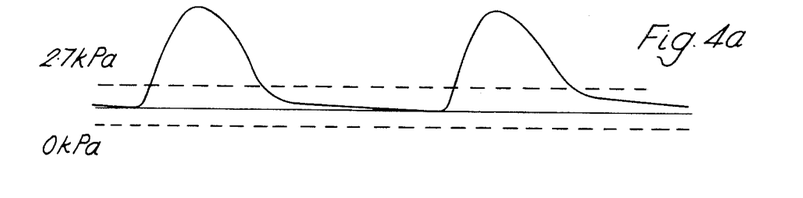
Figure 4B:
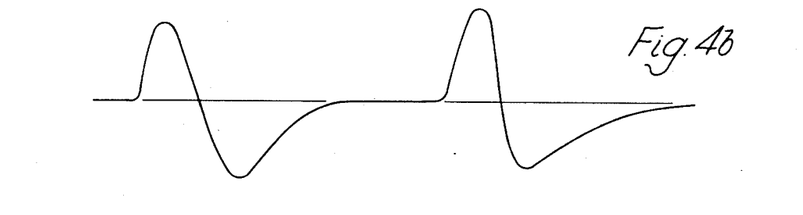
Figure 4C:
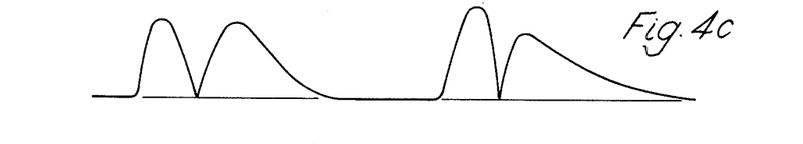
Figure 4D:
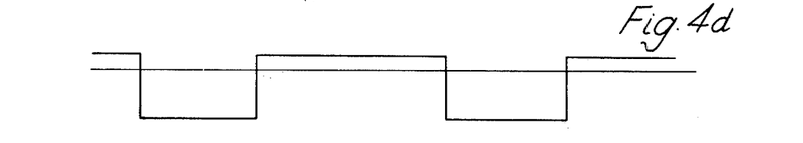
Figure 4E:
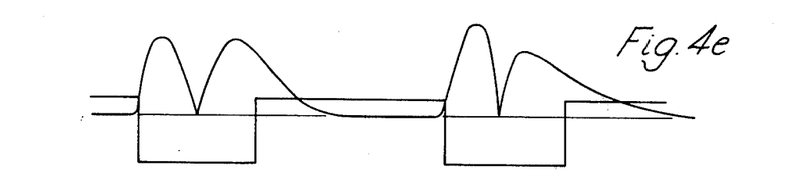

To obtain the switching signals for the sample-and-hold circuit 38 the pressure versus time signal, shown again in FIG. 4(a) is differentiated by a circuit 40 and then applied to a full-wave rectifier 41 the output signals of these circuits being shown in FIGS. 4(b) and 4(c), respectively. A comparator 42 controlling the switching of the circuit 38 receives the rectified and differentiated pressure signal which it compares with a reference signal derived by a comparator 43. The comparator 43 changes state when the pressure exceeds 2.7 kPa and its output signal is therefore as shown in FIG. 4(d). When the rectified differentiated pressure signal is greater than the output from the comparator 43 at the beginning of a contraction (see FIG. 4(e)), the comparator 42 switches the circuit 38 to "hold", and the circuit is switched back to "sample" when the contraction dies away and a signal from the comparator 43 again exceeds that from the rectifier 41. The object of using the comparator 43 is to avoid the circuit 38 switching back to "sample" when the differentiated pressure signal is zero at the peak of a contraction.

The output of the comparator 42 appearing at a terminal 44 is used, as will be explained later, to trigger the alarm circuit 17 and the artefact suppression circuit 18.

Figure 3B:
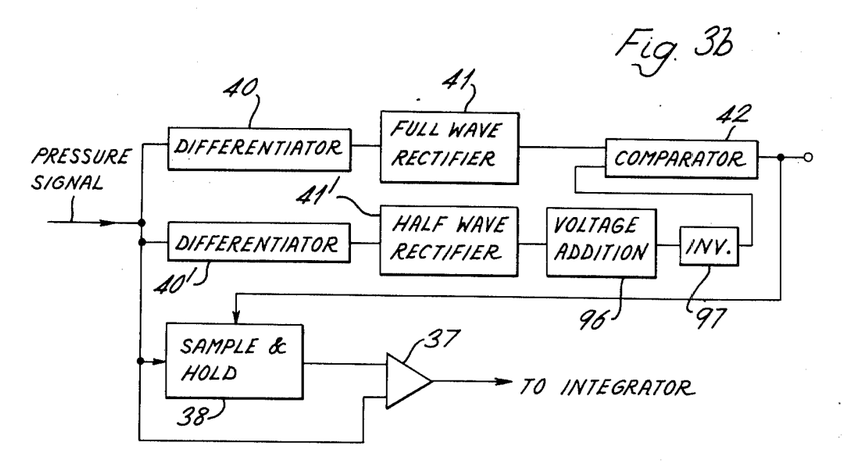

Another baseline correction circuit which may be used as the circuit 13 is shown in FIG. 3b where the comparator 43 of FIG. 3a is replaced by a further differentiator 40' and half-wave rectifier 41, the further differentiator 40' having a longer time constant than the differentiator 40. The two differentiators have different time constants so that the zero differentiator outputs resulting from maximum pressure do not occur at the same time. Different time constants are achieved by using components having different resistance and/or capacitance values. A reference voltage equivalent to 1.3 kPa is added to the signal from the further halfwave rectifier 41' in a circuit 96 and the resultant signal is passed to an inverter 97 before application to the comparator 42. Thus when a contraction commences the signal from the rectifier 41 becomes larger than that from the inverter 97 but as the contraction fades the signal from the inverter 97 becomes larger than the signal from the rectifier 41. Hence the comparator 42 again provides a suitable control signal for the sample and hold circuit 38. This alternative baseline correction circuit provides faster response in recognising onset of contractions and can be used where the pressure transducer is of a type which does not provide a calibrated output signal with a known relationship in terms of kiloPascals and therefore may have a basal pressure reading exceeding the reference voltage equivalent to 2.7 kPa applied to the comparator 43.

The half-wave rectifier may be replaced by a full-wave rectifier and the time constant of the differentiator 40' may be shorter than that of the differentiator 40.

Figure 10:
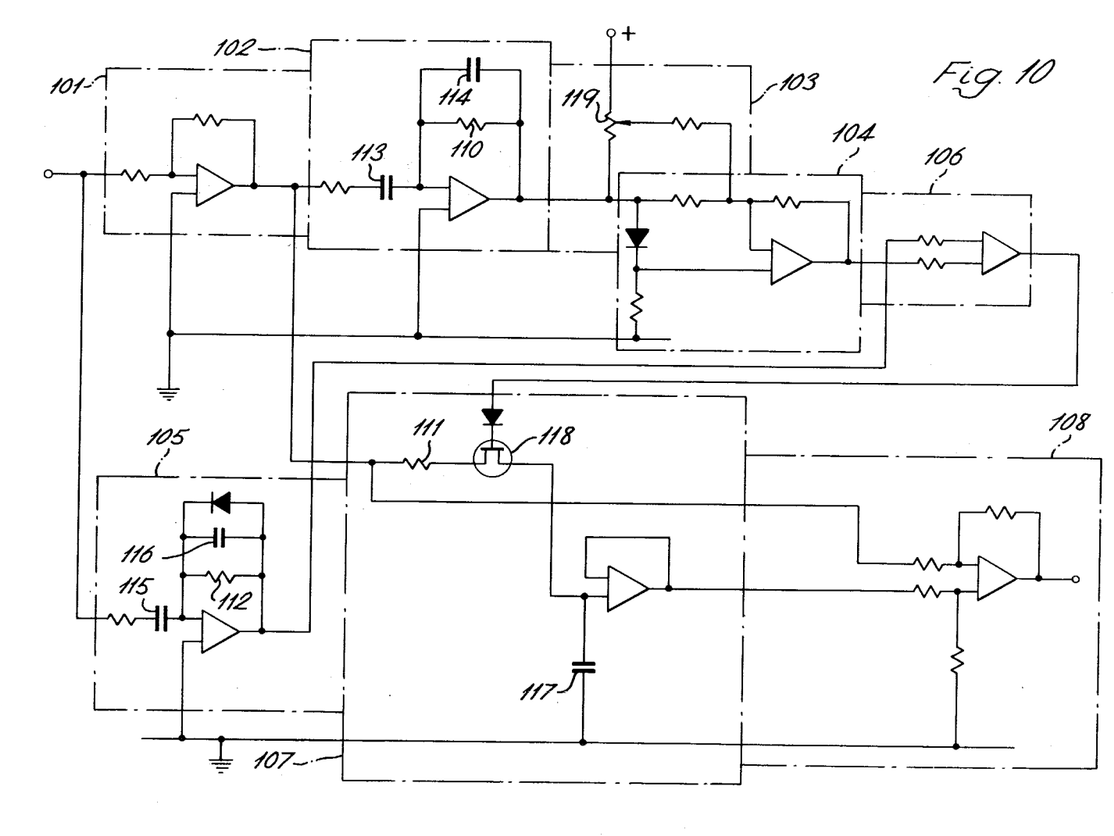
FIG. 10 is a part-block part-circuit diagram of a baseline correction circuit.

The circuit of FIG. 3(b) is shown in more detail with minor modifications in FIG. 10. An inverter 101 is connected to a differentiator 102 followed by a voltage addition circuit 103 and a full-wave rectifier circuit 104, these circuits being equivalent to the circuits 97, 40, 96 and 41, respectively. A differentiator and full-wave rectifier circuit 105 is connected to a comparator 106, whose output is connected to a sample and hold circuit 107. Finally a differential amplifier 108 is connected at the output of the sample and hold circuit and to receive the pressure signal from the inverter 101. The equivalence to FIG. 3(b) will be apparent, the voltage addition and inverter circuits being connected to the differentiator 40 and the full-wave rectifier 41 instead of the circuits 40' and 41', and both input signals to the differential amplifier 108 being inverted.

In FIG. 10 all resistors are 10 K ohm except resistors 110, 111 and 112 which are 1 M ohm, 330 K ohm and 2.2 M ohm, respectively, and all amplifiers shown as included in the various circuits are type 741 except that of the sample and hold circuit 107 which is an FET amplifier (for example National Semiconductor LH 0022 series, operational amplifier). Capacitors 113 to 117 have values 122μF., 0.68μF., 200μF., 4.7μF. and 2.2μF., respectively. FET 118 is type P1086E and the potentiometer 119 has a maximum value of 10K ohms.

When a short duration artefact occurs in the pressure signal, the output signal appearing at terminal 44 of FIG. 3 switches the monostable circuit 18 to its unstable condition and isolates the input of the integrator 16 by switching off a field effect transistor (FET) (not shown) which forms the switch means 19. The circuit 18 remains in its unstable state for two seconds and then switches on the FET reconnecting the integrating circuit. Since as can be seen from FIG. 2 a large number of short duration artefacts occur their total area would give rise to considerable error if the signal reaching the integrator contained the artefacts. On the other hand although a two second interruption in the connection to the integrator 16 occurs each time a contraction takes place, the error in integrated output signal is small since the two seconds duration of this interruption is small compared with the length of a contraction which is usually about a minute.

Figure 4F:
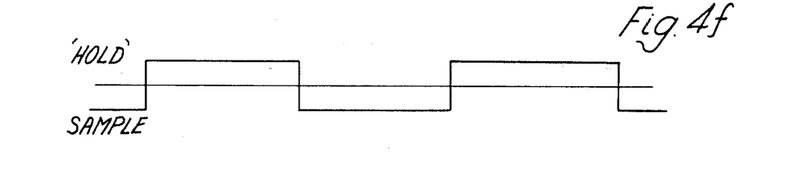
Figure 4G:
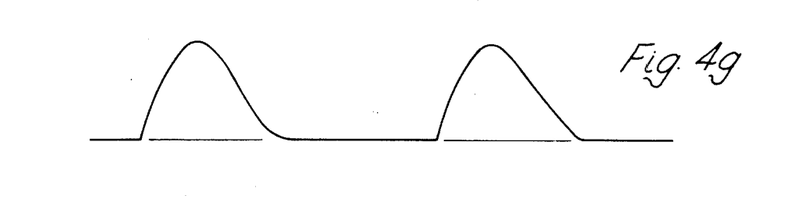

When the patient is placed on a bedpan the switch 21a is manually operated and the state of a bistable circuit 21(b) changes applying a signal to a gate (not shown) which receives as another input, a signal from a comparator, such as the comparator 43 in FIG. 3a. Thus, provided the pressure exceeds 2.7 kPa, an FET (not shown) which forms the switch means 21c then isolates the input of the integrator circuit 16. At the same time a clock pulse oscillator (not shown) in the timer 22 is switched off so suspending the interval for which integration is carried out while intrauterine pressure is abnormally high. When the pressure returns to below 2.7 kPa the trailing edge of the pulse (see FIG. 4f) which appears at the terminal 44 resets the bistable circuit 21b reconnecting the input signal to the integrator and restarting the timer 22.

Figure 5:
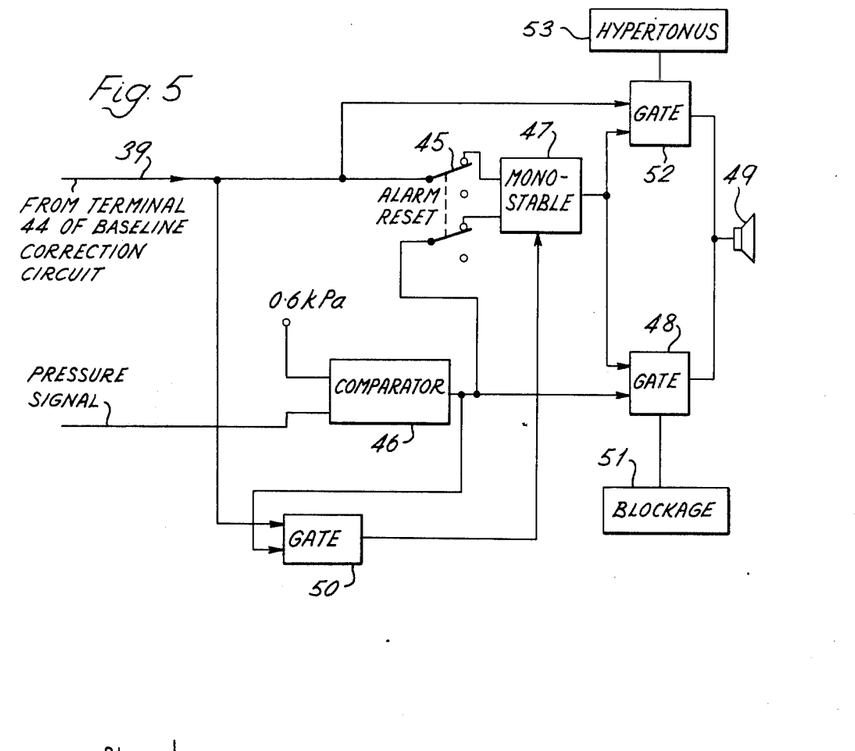
FIG. 5 is a block diagram of the alarm systems of FIG. 1.

The alarm circuit 17 will now be described in more detail with reference to FIG. 5. If the catheter which forms part of the pressure transducer becomes blocked the pressure signal drops to about zero. Since the pressure signal is supplied to a comparator 46 which also receives a reference voltage equivalent to 0.6 kPa, the comparator sets a monostable circuit 47 to its unstable state when the pressure drops to below 0.6 kPa. The output signal from the comparator 46 also passes to a gate 48 but it is not gated to an alarm 49 until the gate 48 receives a signal from the monostable circuit 47. The signal is provided when the monostable returns to its stable state after ninety seconds so that if the abnormal low pressure lasts for more than ninety seconds the alarm 49 is sounded. At the same time the comparator output signal is gated to a display 51 indicating that a blockage has occurred.

The output from terminal 44 of the comparator 42 (shown in FIG. 3a) is also connected by way of a connection 39 to change the monostable circuit 47 to its unstable state. Thus when hypertonus occurs and the basal pressure is raised above 2.7 kPa, a signal is applied to a gate 52 and if the hypertonus continues for more than 90 seconds the signal from the terminal 44 is gated to the alarm circuit 49, causing the alarm to sound. At the same time this signal is gated to a display 53 which indicated hypertonus. When the circuit of FIG. 3b is used, the output of a further comparator (not shown) is applied by way of the connection 39 to the monostable circuit 47. The pressure signal and a reference signal equivalent to 2.7 kPa are applied as inputs to the further comparator.

Both alarm circuits are reset by operating an alarm reset switch 45 so that the monostable circuit 47 is triggered to its unstable state closing the gates 48 and 52. The alarms cannot therefore be disabled, only reset every 90 seconds.

If during the ninety second interval following the operation of the switch 45 in resetting the alarm, a high pressure condition returns to below 2.7 kPa and then a contraction occurs again raising pressure, the alarm would sound again if it were not for the provision of a gate 50. If either alarm condition temporarily ceases as sensed by the gate 50, while the ninety second interval occurs, the monostable circuit 47 is immediately set by the gate 50 to its stable state. Hence the alarm will then not sound again unless an alarm condition still exists 90 seconds after the monostable circuit 47 is re-triggered for example by a new contraction.

The programming and operation of the PROM 31 according to the algorithm shown in FIG. 6, will now be explained. Progress through this algorithm is controlled by the output signals of the comparator circuits 26, 27 and 28 as each new integrator output signal is read into the sample-and-hold circuit 23, the previous contents of this circuit is shifted through the sample-and-hold circuits 24 and 25.

The initial oxytocin dose should be between 0 milli units/ minute (m U/min) and 4m U/min, preferably 2 m U/min where the Unit is an international unit equal to 0.5 gms of dried posterior pituitary gland of an ox.

Figure 6:
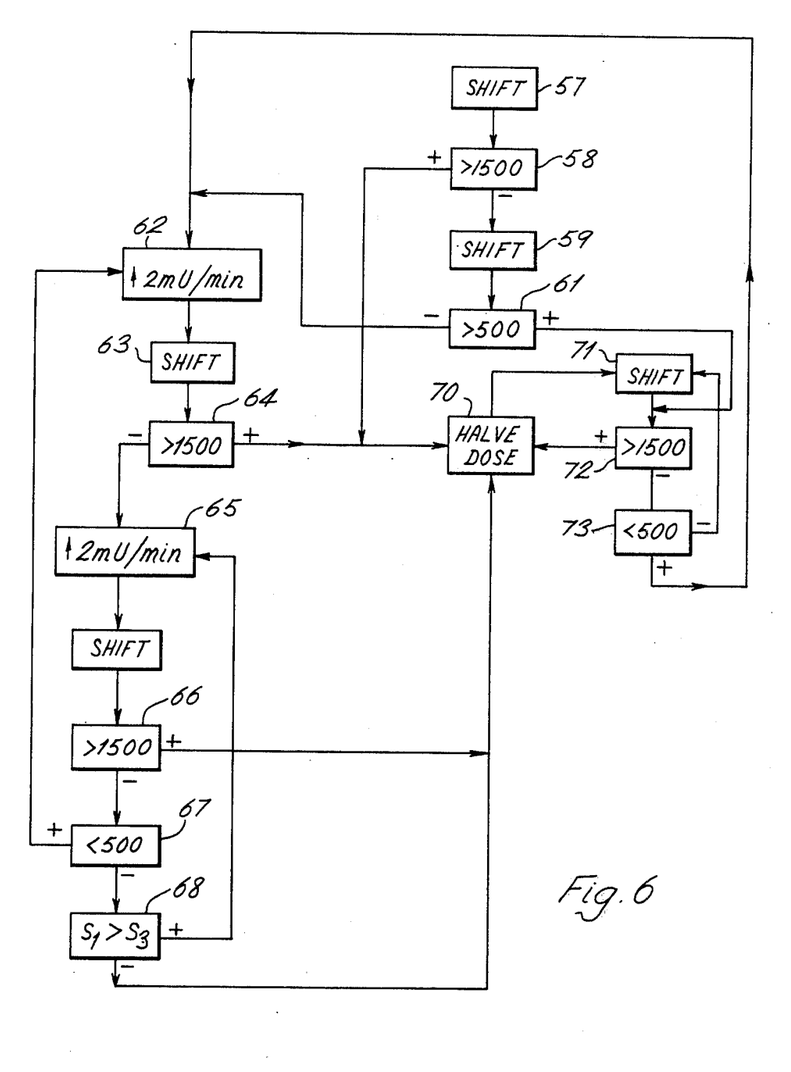
FIG. 6 is an algorithm for programming the PROM of FIG. 1.
Figure 7:
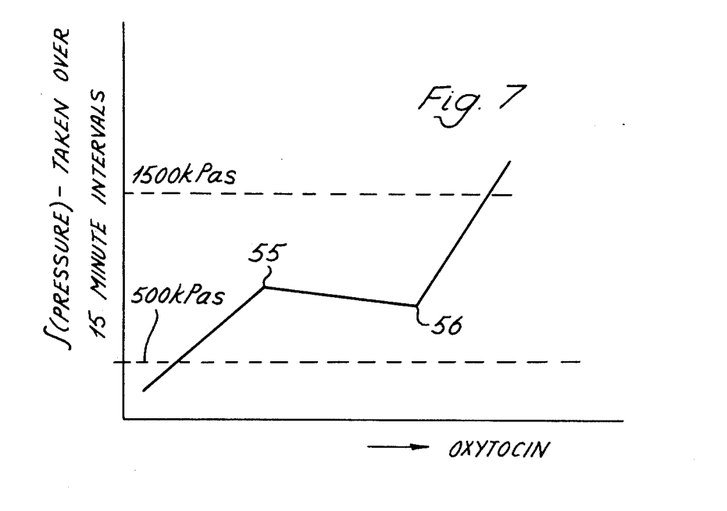
FIG. 7 is a graph showing the integral of pressure versus rate of infusion of oxytocin.

The algorithm if FIG. 6 is based on the integral of pressure, taken over fifteen minute intervals, versus rate of infusion of oxytocin curve shown in FIG. 7. The curve shown is idealised and assumes a steadily increasing rate of infusion. As dosage is increased the integral of pressure rises steadily until a "knee" is reached at point 55. The incremental dose should be between 1m U/min/15 min and 4m U/min/15 min, preferably 2m U/min/15 min.

There is then a slight drop in the integral until a sharp rise occurs at point 56. If the point 56 is passed the combination of pressure in contractions and frequency of contractions implied by the integral of pressure curve may mean that the foetus suffers from lack of oxygen.

The rate of infusion can be stabilised at the point 55 and in fact the rate of infusion of oxytocin can be halved when the point 55 is reached without reducing the progress of labour significantly. In practice it has been found that the dosage should be reduced by an amount not less than one quarter and not more than three quarters of the current dose, preferably by one half. Thus the algorithm of FIG. 6 depends on detecting the point 55 and reducing the rate of infusion by half when detection occurs.

However certain safeguards need to be built into the algorithm. The inventors have found by statistical study that the integral must reach 500 kPas before labour can be said to have commenced and that the integral must be kept above this figure to ensure steady progress. Again it has been discovered that in most cases it is dangerous for the foetus to allow the integral of pressure to rise above 1500 kPas. Both these figures therefore mark significant tests carried out at different points in the algorithm.

A typical progression through the algorithm will now be described. When the first output signal from the integrator 16 is shifted to the sample-and-hold circuit 23 the algorithm is entered at point 57 and a test 58 is carried out to determine whether the integral is greater than 1500 kPas. Normally the integral will be below this figure so that when the next integrator output signal occurs and is passed to the sample-and-hold circuit 23, while the contents of that circuit are passed to the circuit 24 as indicated by "shift" at 59, a test 61 will be carried out to determine whether the new integral is less than 500 kPas. At this stage the left-hand branch at 61 will usually be taken and the dose will be increased by 2m U/min as indicated at 62. When the next shift occurs at 63, a test 64 is carried out to determine again whether the new integral is less than 1500 kPas. If so the dose is again increased by 2m U/min at 65. A further test to determine whether the next integral is below 1500 kPas is carried out at 66 followed by a test at 67 for an integral less than 500 kPas. Again at this stage it is assumed that the integral is below this figure and the dose is again increased by returning to the point 62. The portion 62 to 67 of the algorithm is then cycled as long as is necessary for the test 67 to indicate that the integral has risen above 500 kPas. When this occurs a test is carried out at 68 to determine whether the current integral $S_1$ is greater than that which occurred half an hour previously and is now the contents $S_3$ of the sample-and-hold circuit 25. Usually the point 55 in FIG. 7 will not have been reached the first time the test 68 is carried out so that the portion of the algorithm 65, 66, 67 and 68 is repeated until $S_1$ is less than $S_3$ indicating that the point 55 has been reached. At this time the oxytocin dose is halved at 70 and then following the next shift 71 two tests 72 and 73 are carried out to ensure that the current integral is not greater than 1500 kPas or less than 500 kPas and if both these conditions are fulfilled the dose remains stable while the algorithm cycles through the portion 71, 72 and 73. At points 58, 64, 66 and 72 the safety measure of reducing to half dose is provided if the current integral is greater than 1500 kPas. Test 73 ensures that labour progresses by increasing the dose and returning to point 62 if the current integral falls below 500 kPas. Should the current integral exceed 500 kPas at 61, which is normally early on in induced labour, the stable portion 71, 72, 73 of the algorithm is entered directly at 71.

Figure 8:
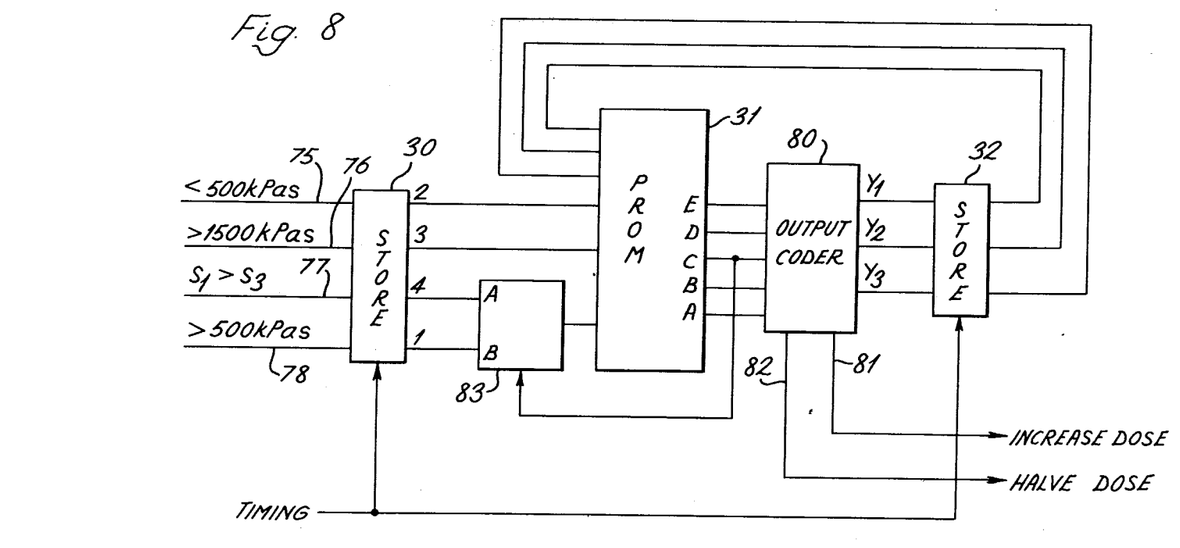
FIG. 8 is a block diagram of the PROM of FIG. 1.

In order to simplify FIG. 1, an output coder 80 and a selection circuit 83 used with the PROM 31 are omitted and shown only in FIG. 8.

When the first integrated output signal from the circuit 16 reaches the sample-and-hold circuit 23 the outputs from the comparators 26, 27 and 28, and the inverter 29 are entered into the store 30 along the four input lines 75 to 78, respectively. These four input signals are immediately passed to output lines 1, 3, 4 and 2, respectively, which also appear as column headings under "comparator output" in Table I (see below) which is the truth table for the PROM 31. If the current integral is not greater than 1500 kPas comparator output 3 will be zero and an output will appear on terminal A of the PROM. Referring now to Table II (see below) which is the truth table for the output coder 80, it will be seen that under these conditions a 1 appears at a terminal $Y_3$ of the coder. The signals appearing on terminals $Y_1$, $Y_2$ and $Y_3$ are stored by the store 32 and passed back to input terminals of the PROM, Table I having columns headed $Y_1$, $Y_2$ and $Y_3$.

TABLE I

| Position In Algorithm | Coded Output From Prom | | | Comparator Output | | | Output From Prom | | | | |
|---|---|---|---|---|---|---|---|---|---|---|---|
| | $Y_1$ | $Y_2$ | $Y_3$ | 1/4 | 2 | 3 | A | B | C | D | E |
| 57 and 58 | 0 | 0 | 0 | */* | * | 0 | 1 | | | | |
| | 0 | 0 | 0 | */* | * | 1 | | | | 1 | |
| 59 | 0 | 0 | 1 | 0/* | * | * | | 1 | | | |
| 61 and 72 | 0 | 0 | 1 | 1/* | 0 | 0 | | | | | 1 |
| | 0 | 0 | 1 | 1/* | 0 | 1 | | | | 1 | |
| 63 and 64 | 0 | 1 | 0 | */* | * | 0 | | | 1 | | |
| | 0 | 1 | 0 | */* | * | 1 | | 1 | | | |
| 66 to 68 | 0 | 1 | 1 | */* | * | 1 | | | | 1 | |
| | 0 | 1 | 1 | */* | 1 | 0 | 1 | | | | |
| | 0 | 1 | 1 | */0 | 0 | 0 | | | | | 1 |
| | 0 | 1 | 1 | */1 | 0 | 0 | | | 1 | | |
| 72 and 73 | 1 | 0 | 0 | */* | * | 1 | | 1 | | | |
| | 1 | 0 | 0 | */* | 0 | 0 | | | | | 1 |
| | 1 | 0 | 0 | */* | 1 | 0 | 1 | | | | |
| 72 and 73 | 1 | 0 | 1 | */* | * | 1 | | | | 1 | |
| | 1 | 0 | 1 | */* | 0 | 0 | | | | | 1 |
| | 1 | 0 | 1 | */* | 1 | 0 | 1 | | | | |

TABLE II

| PROM OUTPUT | | | | | CODED FEEDBACK SIGNAL | | |
|---|---|---|---|---|---|---|---|
| A | B | C | D | E | $Y_1$ | $Y_2$ | $Y_3$ |
| 0 | 0 | 0 | 0 | 0 | 0 | 0 | 0 |
| 1 | 0 | 0 | 0 | 0 | 0 | 0 | 1 |
| 0 | 1 | 0 | 0 | 0 | 0 | 1 | 0 |
| 0 | 0 | 1 | 0 | 0 | 0 | 1 | 1 |
| 0 | 0 | 0 | 1 | 0 | 1 | 0 | 0 |
| 0 | 0 | 0 | 0 | 1 | 1 | 0 | 1 |

In Table I "1" indicates a high level in positive logic, "0" indicates a low level and * indicates that the state is irrelevant.

It will now be clear how the algorithm of FIG. 6 is put into effect since each time a shift occurs a new set of inputs appear for the PROM and the outputs obtained from the PROM which depend on the program entered therein also appear at the terminals A to E. These signals when applied to the ROM 80 provide new feedback signals and where appropriate provide command signals on connections 81 and 82 to increase or halve the dose, respectively. Whenever the B output or C output occurs a signal appears on the connection 81 to increase the dose by 2m U/min and whenever the D output occurs a signal appears on the connection 82 to halve the dose.

Thus as the various inputs for the PROM change in accordance with the outputs of the comparators 26, 27 and 28 and the signals fed back by way of the store 32 (representing the current position in the algorithm), progress is made through the algorithm. Table I can be related to the algorithm by using the first column of the table.

For example, after the dose has been increased at 65 and a shift has occurred, test 66 in the algorithm is reached. If the current activity signal is greater than 1500 kPas as indicated by input 3 being a one, then regardless of other inputs to the PROM from other comparators, the dose must be halved so output D is given. If on the other hand the current activity signal is less than 1500 kPas, as indicated by input 3 being zero, test 67 can be carried out. If input 2 is one, a return to test 62 is made but if input 2 is zero test 68 is made in dependence on input 4 and either the dose is increased (an output at B) or halved (an output at D). Since this example will have made clear how the algorithm of FIG. 6 progresses, no further examples are given.

Suitable circuits for the PROM are Texas Instruments Programmable Read-Only Memories Types SN 54186 or SN 74186 and these can be programmed according to the makers' instructions to provide the required outputs according to Table I. The stores 30 and 32 may be Texas Instruments four-bit latches type Ser. No. 54116 or Ser. No. 74116, and the output coder 80 may be constructed from four NOR gates of Texas Instruments type Ser. No. 5432 or Ser. No. 7432.

Either the output from comparator 28 or from the comparator 26, by way of the store 30, are passed to one input of the PROM 31. This selection is achieved by means of a circuit 83 which selects the inverter output when the PROM output C is high. It will be apparent from further study of FIG. 8 and Tables I and II how the remainder of the algorithm of FIG. 6 is put into effect.

Other algorithms may of course by used many of which can be put into operation simply by changing the programming of the PROM rather than substituting different circuits. A modification which can be made to the algorithm of FIG. 6 is to take the $S_1$ not greater than $S_3$ output of test 68 to a further "halve dose" operation (not shown) and then back to point 59.

The invention can also be put into practice when the signal representative of intrauterine pressure is a digital signal. The baseline correction circuit, the integrator, the sample and hold circuits and the comparator circuits of FIG. 1 are then digital circuits. Integration is carried out digitally and the sample and hold circuits may be replaced by digital stores, for example types Ser. No. 54116 or Ser. No. 74116. The comparators may then be digital types Ser. No. 5485 or Ser. No. 7485. Clearly digital signals and circuits can be introduced at any point in the circuit of FIG. 1 and as an example it is convenient to use an integrator of the type which receives an analog input signal but has a digital output signal.

Figure 9:
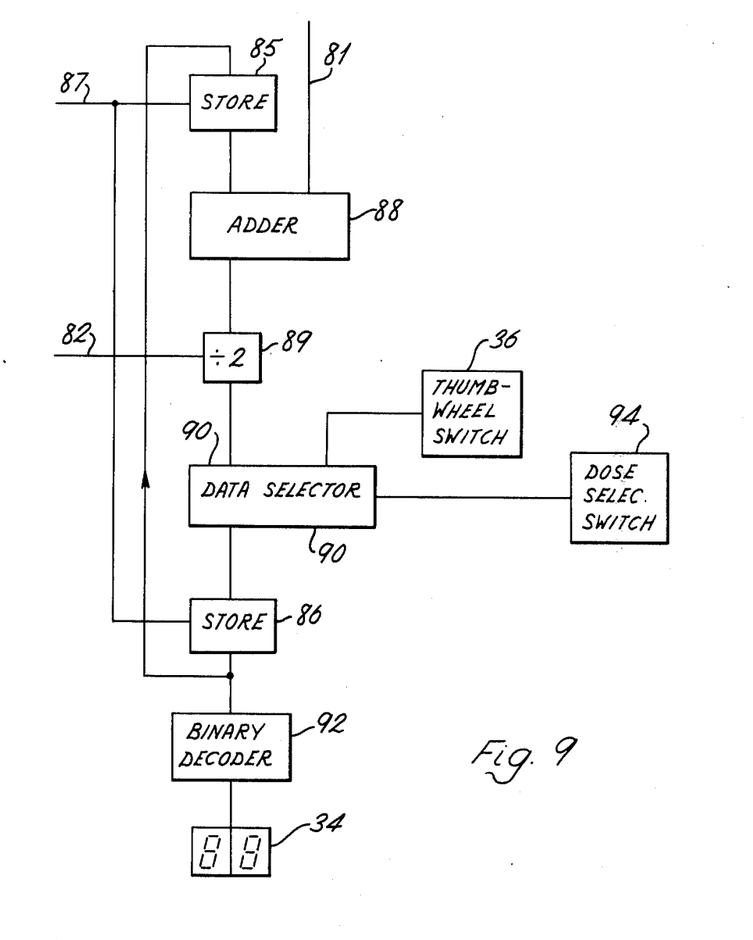
FIG. 9 is a block diagram of the dosage calculator of FIG. 1.

The output from the PROM 31 controls the dose calculator 33 which is shown in more detail in FIG. 9. At switch-on, two stores 85 and 86 are cleared and at the end of each timing period as signalled along a channel 87 from the time 22, the contents of the store 86 are applied by way of the store 85 to an adder circuit 88. If now the signal on connection 81 from the ROM output 80 of FIG. 8 indicates that "2" should be added, the adder circuit carries out the addition and passes its output by way of a divide-by-two circuit 89 and a data selector 90 back to the store 86. When 2m U/min are to be added to the dose as in this sequence of operations the divide-by-two circuit 89 is inactive since it is never required to divide at the same time as the dose is increased. However at other points in the algorithm there will be no command on the connection 81 to add, but rather a command on the connection 82 to divide-by-two and this will be carried out by circuit 89.

Thus it will be seen that the current dose is stored by the circuit 86 and it is the output of this circuit which controls the digital read-out 34 by way of a binary to seven-segment decoder 92.

The contents of the store 86 also control the pump 35 by way of a digital-to-analogue converter (not shown).

Should it be required to set the dose to a particular value, this can be carried out by using the thumbwheel switch 36. The switch is set to the value required and then a dose select switch 94 is operated manually so that the value represented by the setting of the switch 36 is entered by way of the data selector 90 into the store 86.

The timer 22 is controlled by a clock pulse oscillator (not shown) with a repetition period of 0.9 seconds but this is divided by a thousand to give a timing period of 900 seconds. At the end of each 900 second period a number of sequential timing pulses each of 0.9 seconds duration are provided and supplied as required to the sample-and-hold circuit 23 to sample the integrator output, to the sample-and-hold circuits 24 and 25, the stores 30 and 32 and the dose calculator 33 to ensure that data is transferred as required in the foregoing description. Since the transfer of data items by sequential pulsing of circuits is well known it will not be described further except to mention that conventional arrangements are also made for clearing or resetting the various circuits mentioned and for providing the required selection of sequential timing pulses to allow the setting of the thumbwheel switch 36 to be entered into the dose calculator 33. Where the integrator 16 provides a digital output the duration of the timing pulses is preferably reduced to, for example, 27.5 milliseconds.

Although an embodiment of the invention has been specifically described it will be clear that the invention may be put into practice in many other ways. For example the algorithms mentioned can be changed, the programming of the PROM may also be changed and various portions of the circuit of FIG. 1 can be replaced by others having substantially the same function. The PROM may be replaced by a read-only memory constructed to operate a suitable algorithm. The apparatus and/or the algorithm may be modified, for example by modifying the comparator 28 to provide an output signal for equal input signals, to stabilise or reduce the dosage when successive integrals are equal. While the invention is particularly useful in controlling the progress of human births it may also find application at the births of animals.

We claim:

1. Apparatus for indicating uterine activity in labour including:
    means adapted to be coupled to a uterine pressure transducer for providing a first signal representative of intrauterine pressure,
    means for providing a second signal which is equal to the first signal except when a contraction occurs when it takes up a value equal to that of the first signal in the absence of the contraction,
    means for substracting the second signal from the first signal, to provide a third signal, and
    means for integrating the third signal over intervals of at least ten but not more than thirty minutes to provide an activity signal indicative of uterine activity in labour.

2. Apparatus according to claim 1 wherein the first and second signals are analog signals.

3. Apparatus according to claim 1 wherein the means for providing the second signal includes means for holding, during each contraction, a signal equal to the first signal at the beginning of the contraction, the signal held forming the second signal during contractions.

4. Apparatus according to claim 1 wherein the means for providing the second signal include
    detection means for detecting first and second changes in the first signal likely to be indicative of the onset and completion, respectively, of a contraction, and
    a sample-and-hold circuit for sampling the first signal except between the detection of said first and subsequent second changes by the detection means when the last value sampled is held, the output of the sample and hold circuit providing the said second signal.

5. Apparatus according to claim 4 wherein the detection means includes a differentiation circuit with output coupled to a first input of a first comparator by way of a full-wave rectifier circuit, and
    gating means for applying a signal to a second input of the first comparator which is of opposite polarity to output signals of the full-wave rectifier circuit when the rate of change of the first signal falls to zero during a contraction,
    the first comparator providing signals maintaining the sample-and-hold circuit in its hold state whenever the signal applied to the first comparator is of the same polarity as and greater than that applied to its second input and when the applied signals are of opposite polarities.

6. Apparatus accoring to claim 5 wherein the gating means includes a second comparator connected to receive the said first signal as one input and a reference signal representative of an intrauterine pressure usually only attained near the beginning of a contraction as another input, the output of the second comparator forming the second input for the first comparator.

7. Apparatus according to claim 5 wherein the gating means includes
    a further differentiation circuit,
    a half-wave rectifier circuit with input coupled to the output of the further differentiation circuit,
    an addition circuit for adding a reference signal to the output of the further full-wave rectifier circuit, the reference signal being representative of an intrauterine pressure usually only attained near the beginning of a contraction, and
    an inverter for inverting the output signal of the addition circuit and applying the inverted signal to the second input of the first comparator.

8. Apparatus according to claim 1 wherein the third signal is integrated over approximately 15 minutes.

9. Apparatus for automatically calculating the dosage of a labour stimulating substance including
    activity-indicating means, adapted to be coupled to a uterine pressure transducer, for providing an activity signal representative of the integral of the additional intrauterine pressure which occurs during contractions above the pressure existing between contractions, the said integral being taken over at least 10 but not more than 30 minutes, first comparison means for comparing the most recently obtained value of an activity signal with the value of a recently obtained previous activity signal, and dose calculating means for determining the dosage of a labour stimulating substance in dependence upon values of the activity signal and for stabilising or reducing the dosage, at least when the value of the activity signal is above a predetermined minimum and below a predetermined maximum, if the first comparison means indicates that the said most recently obtained value of the activity signal is equal to or less than the said recently-obtained previous value of the activity signal, the dosage being so calculated, in operation, that when employed in stimulating labour, labour progresses without substantial interruption and without the activity signal exceeding a dangerous value.

10. Apparatus according to claim 9 including second comparison means for comparing a recent value of the activity signal with a first reference signal representing an upper limit for the values of the activity signal which it is dangerous to exceed, the dose calculating means being coupled to the second comparison means and constructed to stabilize or reduce the calculated dosage when the upper limit is exceeded.

11. Apparatus according to claim 10 wherein the first reference signal is equivalent to an activity signal value of about 1500 kPas.

12. Apparatus according to claim 10 including third comparison means for comparing a recent value of the activity signal with a second reference signal representing a lower limit for the values of activity signals corresponding to a possibility of labour ceasing, the dose calculating means being coupled to the third comparison menas and constructed to increase the dosage if the lower limit is not exceeded.

13. Apparatus according to claim 12 wherein the second reference signal is equivalent to an activity signal value of about 500 kPas.

14. Apparatus according to claim 10 wherein the activity indicating means includes means adapted to be coupled to a uterine pressure transducer for providing a first signal representative of intrauterine pressure, means for providing a second signal which is equal to the first signal except when a contraction occurs when it takes up a value equal to that of the first signal in the absence of the contraction, means for subtracting the second signal from the first signal, to provide a third signal, and means for integrating the third signal over intervals of at least 10 but not more than thirty minutes to provide the activity signals.

15. Apparatus according to claim 10 wherein the dose calculating means includes a read-only memory or a programmable read-only memory programmed according to an algorithm for determining the dosage which takes account of the values of recent activity signals.

16. Apparatus according to claim 15 wherein at, at least one point in the said algorithm, the dosage determined is stabilized or reduced if a later activity signal is equal to, or less than, an earlier activity signal.

17. Apparatus according to claim 16 wherein the said algorithm is such that at, at least one point therein, the dosage determined is stabilized or reduced if the value of a recent activity signal exceeds an upper limit for integral signals which it is dangerous to exceed.

18. Apparatus according to claim 17 wherein the said algorithm is such that at, at least one point therein, the dosage determined is increased if the value of a recent activity signal is below a lower limit for integral signals indicating that labour may cease.

19. Apparatus according to claim 10 wherein the dose-calculating means is coupled to dispensing means for controlling the rate of infusion of a labour stimulating substance into a patient.

20. Apparatus for deriving a corrected signal from a signal with a varying datum, including means for receiving a first signal having a varying datum, means for providing a second signal which is equal to the first signal except when the first signal deviates from the datum when it takes up a value equal to that of the first signal in the absence of deviation, including detection means for detecting first and second changes in the first signal likely to be indicative of the onset and completion, respectively, of deviation from the datum, and a sample-and-hold circuit for sampling the first signal except between the detection of said first and subsequent second changes by the detection means when the last value sampled is held, the output of the sample and hold circuit providing the said second signal, said detection means further including a differentiation circuit with output coupled to a first input of a first comparator by way of a full-wave rectifier circuit, and gating means for applying a signal to a second input of the first comparator which is of opposite polarity to output signals of the full-wave rectifier circuit when the rate of change of the first signal falls to zero during deviation from the datum, the first comparator providing signals maintaining the sample-and-hold circuit in its hold state whenever the signal applied to the first comparator is of the same polarity as the greater than that applied to its second input and when the applied signals are of opposite polarities, and means for providing a third corrected signal by subtracting the second signal from the first signal.

21. Apparatus according to claim 20 wherein the gating means includes a second comparator connected to receive the said first signal as one input and a reference signal representative of a value of the first signal usually only attained near the beginning of a deviation from the datum as another input, the output of the second comparator forming the second input for the first comparator.

22. Apparatus according to claim 20 wherein the gating means includes a further differentiation circuit, a half-wave rectifier circuit with input coupled to the output of the further differentiation circuit, an addition circuit for adding a reference signal to the output of the further full-wave rectifier circuit, the reference signal being representative of a value of the first signal usually only attained near the beginning of a deviation from the datum, and an inverter for inverting the output signal of the addition circuit and applying the inverted signal to the second input of the first comparator.

* * * * *